(12) United States Patent
Mansfield

(10) Patent No.: US 8,374,312 B2
(45) Date of Patent: Feb. 12, 2013

(54) PRONE PATIENT POSITIONING DEVICES AND METHODS

(75) Inventor: Stanley Mansfield, Sunnyvale, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 250 days.

(21) Appl. No.: 12/708,273

(22) Filed: Feb. 18, 2010

(65) Prior Publication Data

US 2011/0200178 A1 Aug. 18, 2011

(51) Int. Cl.
*A61B 6/04* (2006.01)
*A61N 5/10* (2006.01)

(52) U.S. Cl. .............. 378/65; 378/20; 378/37; 378/209; 5/601

(58) Field of Classification Search .............. 378/20, 378/37, 65, 208, 209; 5/601
See application file for complete search history.

(56) References Cited

U.S. PATENT DOCUMENTS

| | | | |
|---|---|---|---|
| 5,289,520 A * | 2/1994 | Pellegrino et al. ............... 378/37 |
| 5,564,438 A | 10/1996 | Merchant |
| 5,727,554 A | 3/1998 | Kalend et al. |
| 5,778,047 A | 7/1998 | Mansfield et al. |
| 6,419,390 B1 * | 7/2002 | Landis-Lowell ............... 378/209 |
| 6,446,286 B1 * | 9/2002 | Karmalawy ........................ 5/601 |
| 6,922,859 B2 | 8/2005 | Gagnon et al. ..................... 5/601 |
| 6,987,831 B2 * | 1/2006 | Ning ................................ 378/37 |
| 7,017,209 B1 * | 3/2006 | De Jong et al. .................... 5/601 |
| 7,076,821 B2 * | 7/2006 | de Mooy ............................ 5/601 |
| 7,450,688 B2 * | 11/2008 | Becker et al. .................... 378/68 |
| 7,540,661 B2 * | 6/2009 | Hornig ............................ 378/209 |
| 7,694,370 B1 * | 4/2010 | Lee ..................................... 5/632 |
| 7,763,864 B2 * | 7/2010 | Formenti ................... 250/453.11 |
| 7,864,918 B2 * | 1/2011 | Schilling et al. ................ 378/37 |
| 7,957,508 B2 * | 6/2011 | Brooks et al. ................... 378/65 |
| 8,146,186 B2 * | 4/2012 | Diao ................................ 5/601 |
| 2007/0032795 A1 | 2/2007 | Schloesser et al. |
| 2007/0033735 A1 | 2/2007 | Formenti |
| 2008/0043905 A1 * | 2/2008 | Hassanpourgol ............... 378/37 |
| 2008/0201850 A1 * | 8/2008 | Brito et al. ......................... 5/601 |
| 2008/0240353 A1 | 10/2008 | Myles |
| 2009/0013468 A1 | 1/2009 | Bourne et al. |
| 2011/0047702 A1 * | 3/2011 | Diao ................................ 5/601 |

FOREIGN PATENT DOCUMENTS

WO 0007669 A1 2/2000

OTHER PUBLICATIONS

PCT, International Search Report and Written Opinion in International Application No. PCT/US2011/024433, Oct. 27, 2011, 9 pages.
Grann et al., "Prone Breast Radiotherapy in Early-Stage Breast Cancer: A Preliminary Analysis," Int. J. Radiation Oncology Biol. Phys., 2000, vol. 47, No. 2, pp. 319-325.
Jozsef et al., "Application of Radiosurgery Principles to a Target in the Breast: a Dosimetric Study," Med. Phys. May 2000, 27(5), pp. 1005-1010.
Clearvue, "Prone Position Breast Radiotherapy System," 2009, 4 pages.

* cited by examiner

*Primary Examiner* — Allen C. Ho
(74) *Attorney, Agent, or Firm* — Houst Consulting

(57) ABSTRACT

A radiotherapy couch top includes a cantilevered section adapted to support at least a portion of a prone patient's upper body. The cantilevered section may be provided with an opening configured to allow at least a portion of the body portion to extend into from above and to allow a radiation beam to pass through from below.

25 Claims, 3 Drawing Sheets

PRONE PATIENT POSITIONING DEVICES AND METHODS

BACKGROUND

This invention relates generally to radiation apparatuses and methods, and in particular to devices for supporting or positioning patients in prone positions for radiotherapy, imaging and/or treatment simulation.

Breast cancer is one of the most common cancers among women in the United States. Each year, about 200,000 American women are diagnosed to have breast cancer. One of eight women born today will be diagnosed with breast cancer at some time during their lifetime. Depending on the type, stage of the cancer and other factors, patients with breast cancer can be treated with radiation therapy, surgery, and other forms of therapy. Radiation therapy in the breast is usually used in conjunction with surgery and may also be combined with chemotherapy. Most patients receive whole-breast irradiation (WBI) therapy after lumpectomy (surgical removal of cancer lumps) to destroy cancerous cells that may remain in the area after lumpectomy. Some patients opt for accelerated partial-breast irradiation (PBI) therapy because of the appealing shorter treatment time.

The vast majority of radiation therapy of breast cancer is carried out with the patient in a supine position due to the ease of access and patient comfort. In this position however, gravity depresses the breast towards the patient's torso and the breast tends to spread laterally over the chest wall. This makes accurate positioning of the breast difficult and complicates the location of internal structures relative to the radiation beam directions required to deliver the prescribed dose to the breast. Treatment planning options are constrained by the greater proximity of the breast to the chest wall and critical organs including the lung and heart. Also, due to the flattened shape of the breast in a supine position, use of devices such as wedge filters, beam spoilers bolus etc. are often required to overcome non-homogeneous dose distribution and skin overdose.

In some situations it is believed desirable for radiation treatment to be carried out with the patient in a prone position so that gravity pulls the breast away from the chest wall. Prone patient set up may minimize radiation doses to the chest wall and critical organs including the heart and lungs, and provide more uniform dose delivery. In addition a prone position results in less motion of the breast caused by respiration.

Conventional supporting devices for prone breast radiotherapy consist of raised platforms or cushions that rest on top of a couch top, which allow the treated breast to hang into the space between the platform or cushion and the couch top. FIG. 6 illustrates a conventional radiation treatment table for prone breast radiotherapy. With these designs, the upper thorax, arms and head are supported by the platform which in turn rests on the couch top below the breast. A raised platform or cushion placed onto a conventional couch top significantly limits the physical clearance for rotating a radiotherapy treatment machine around the patient as required to direct the treatment beam from various directions. Physical and visual access to the breast being treated is also restricted by the presence of the conventional couch top below the breast.

SUMMARY

A radiotherapy couch is provided comprising a base and a couch top supported by the base. The couch top comprises a section extended in a cantilevered manner adapted to support at least a portion of a prone patient's upper body. The cantilevered section is provided with an opening configured to allow at least a portion of the body portion to extend into from above and to allow a radiation beam to pass through from below.

In some embodiments, the extended section is removable from the couch top. In some embodiments, the extended section is an integral portion of the couch top.

In some embodiments, the opening is formed by removing a portion of the extended section.

In one aspect, a radiotherapy couch top is provided for supporting a patient to receive radiation therapy. The couch top includes a section to be supported in a cantilevered manner adapted to support at least a portion of a prone patient's upper body. The section has an opening configured to allow at least a portion of the body portion to extend into from above and to allow a radiation beam to pass through from below. The section may be detachable from the couch top. Alternatively, the section is an integral portion of the couch top. In some embodiments, the opening in the section is configured to allow a prone patient's breast hanging through. The section may be detachable from the couch top and reversibly attachable to the couch top to allow either the left or right breast to hang through. The opening may be generally in U-shape or in O-shape. In some embodiments, one or more immobilization devices may be provided in the section for positioning of the patient. In some embodiments at least one of the immobilization devices may be indexed. In some embodiments at least one immobilization device may be used to position and/or immobilize a breast hanging through the opening.

In another aspect, a radiotherapy couch insert is provided for positioning a body portion of a patient to receive radiation therapy. The couch top insert includes a section adapted to support at least a portion of a prone patient's upper body, and a mechanism for attaching the section to a couch top of a radiotherapy couch to secure the section in a cantilevered manner. The section has an opening configured to allow at least a portion of the body portion to extend into from above and to allow a radiation beam to pass through from below.

In some embodiments, the section has a first portion having the opening configured to allow a prone patient's breast hanging through, and a second portion configured to support the other breast, and the second portion is adjustable with respect to the first portion.

In some embodiments, the couch top insert includes a first opening in the extended section configured to allow a body portion hanging through below the section and a second opening configured to allow a treatment beam to pass through unimpeded. In some embodiments the second opening includes a removable insert configured to fill the second opening when a treatment beam does not pass through the second opening. In some embodiments the second opening is an extension of the first opening.

In some embodiment, a radiotherapy couch includes a base and a couch top supported by the base. The couch top has a first section, a second cantilevered section, and an opening in the cantilevered section or between the cantilevered section and the first section. The cantilevered section has an upper surface configured to support a body portion and a lower surface. The opening is configured to allow at least a portion of the body portion to extend to or below the lower surface of the cantilevered section.

In a further aspect, a radiation method is provided. In the method a patient is positioned in a prone position on a couch top, which has a section extended in a cantilevered manner adapted to support at least a portion of the prone patient's upper body. The section has an opening configured to allow at least a portion of the body portion to extend to or below a lower surface of the cantilevered section. Then a radiation source is positioned relative to the portion of the body portion. Radiation from the source is delivered to at least a portion of the portion extended to or below the lower surface. In some embodiments, the radiation source is a linear accelerator housed in a gantry which is rotatable below the extended section.

In a further aspect, a radiotherapy system includes a radiation source and a couch. The couch comprises a base and a couch top supported by the base. The couch top has a first section, a second cantilevered section, and an opening in the cantilevered section or between the cantilevered section and the first section. The cantilevered section has an upper surface configured to support a body portion and a lower surface. The opening is configured to allow at least a portion of the body portion to extend to or below the lower surface of the cantilevered section. The radiation source is operable to deliver a radiation beam to at least a portion of the portion extended to or below the lower surface of the cantilevered section.

BRIEF DESCRIPTION OF THE DRAWINGS

These and various other features and advantages will become better understood upon reading of the following detailed description in conjunction with the accompanying drawings and the appended claims provided below, where:

DETAILED DESCRIPTION OF EMBODIMENTS

Figure 1:
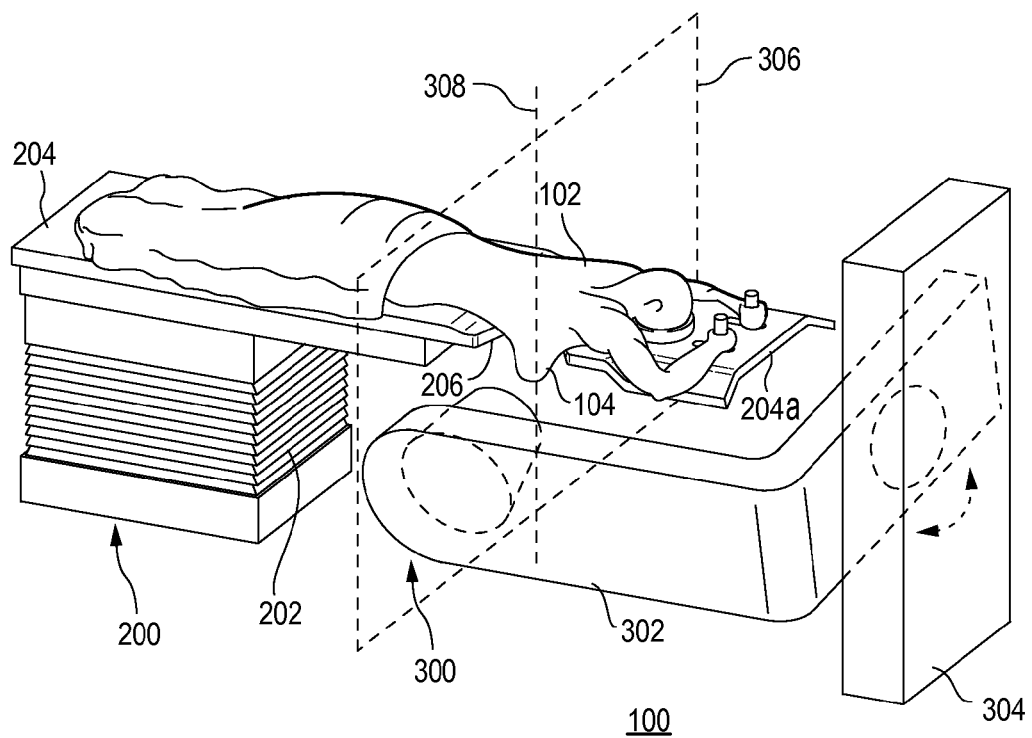
FIG. 1 is a schematic illustrating a treatment couch supporting a prone patient to receive radiotherapy in accordance with some embodiments of the invention.

Various embodiments of prone patient supporting or positioning devices are described. It is to be understood that the invention is not limited to the particular embodiments described as such may, of course, vary. An aspect described in conjunction with a particular embodiment is not necessarily limited to that embodiment and can be practiced in any other embodiments. For instance, the radiotherapy couch, couch top, and couch top insert described herein can be used for supporting or positioning patients in supine or other positions as well as prone positions. The couch, couch top, couch top insert can support or position a patient for treatment simulation, imaging, and therapeutic treatment. Further, while various embodiments are described in connection with linear accelerators, it will be appreciated that the invention can also be practiced in other electromagnetic apparatuses and modalities. It is also to be understood that the terminology used herein is for the purpose of describing particular embodiments only, and is not intended to be limiting since the scope of the invention will be limited only by the appended claims, along with the full scope of equivalents to which such claims are entitled.

In addition, various embodiments are described with reference to the figures. It should be noted that the figures are not drawn to scale, and are only intended to facilitate the description of specific embodiments. They are not intended as an exhaustive description or as a limitation on the scope of the invention.

All technical and scientific terms used herein have the same meaning as commonly understood by one of ordinary skill in the art to which this invention belongs, unless defined otherwise. Various relative terms such as "on," "upper," "above," "top," "over," "below," "under," "bottom," "higher," "lower" or similar terms are used herein in describing relative positions, directions, or spatial relationships in conjunction with the drawings. The relative terms are used only for convenience in description or reference, and should not be so construed as to imply a necessary positioning or directions of the structures or portions thereof or to limit the scope of the invention. As used in the description and appended claims, the singular forms of "a," "an," and "the" include plural references unless the context clearly dictates otherwise.

As used herein, the term radiotherapy includes therapeutic treatment and process or action before or after therapeutic treatment such as radiation simulation or imaging for verification, diagnosis, examination, or treatment planning etc. The term patient includes human, animal or any object under examination.

In general, a radiotherapy couch for supporting a patient particularly a prone patient is provided. The couch includes a couch top having an extended section supported in a cantilevered manner. The extended section supports at least a portion of a patient's upper body such as thorax, arms or head and has an opening for exposing a body portion to radiation beams. The extended section of the couch top allows the breast or a portion of the breast to hang into free or open space, and thus allows multiple beams to pass through the breast at various angles, including at angles that are tangential to the patient's chest wall. The extended section may provide for physical and visual access to the body portion being treated or clearance for a radiotherapy treatment machine around the patient.

FIG. 1 schematically illustrates a radiation system 100 that embodies the principle of the invention. The radiation system 100 includes a couch 200 supporting a patient 102 in a prone position. A radiation source 300 is positioned to deliver radiation to a body portion such as the patient's breast 104. The couch 200 may include a base 202 and a couch top 204. The couch top 204 may be movable relative to the base 202 in the lateral (x-axis) and/or longitudinal (y-axis) directions. The base 202 may be moveable in the vertical directions (z-axis). This would allow the patient 102, which is supported on the couch top 204, to be positioned to a desired location. The couch 200 may also be rotated about an isocenter to provide a different couch angle relative to the radiation source 300. Various mechanisms known in the art including motors, stages, and guides may be used to move the couch or couch top in various directions. The source 300 may be a linear accelerator (LINAC). The accelerator may be configured to generate beams for therapeutic treatment, or imaging, or for both therapeutic treatment and diagnostic imaging. For instance, the accelerator may be operated at beam energy levels ranging from about 2 MV to about 20 MV or higher to generate beams suitable for therapeutic treatment. Alternatively, beam energies up to 1 MV or higher may be desirable for obtaining lower contrast images suitable for positioning. In some embodiments as shown in FIG. 1, the accelerator may be enclosed in a gantry 302 rotatable relative to a supporting stand 304 that may be secured to the floor in a treatment room. In some embodiments, the linear accelerator may be supported on an articulated arm and moved around the patient. The source 300 may also be an X-ray tube mounted to a C-arm or other articulated arm movable around the patient. The source 300 may be configured to generate radiation suitable for therapeutic treatment or imaging. In general, the source 300 can be any source that generates radiation or beams suitable for therapeutic treatment or imaging, including but not limited to X-ray beams, proton beams, electron beams, or other particle beams. The radiotherapy couch 200 provided by the invention allows the source 300 to deliver radiation or beams at various angles to a body portion 104. In some embodiments, the couch 200 allows the source 300 to deliver radiation to the breast 104, or to a portion of the breast 104, at small tangential angles with respect to the chest wall. This allows treatment or imaging of axilla tissue or other soft tissue leading from the breast to the armpit, which is desirable since primary breast cancer lesions often spread to infect lymph nodes in this region.

As shown in FIG. 1, a section 204a of the couch top 204 extends beyond the base 202 and supported in a cantilevered manner. The extended section 204a supports at least a portion of the patient's upper body such as thorax, arm or head. An opening 206 in the extended section 204a allows at least a portion of a body portion such as the patient's breast 104 to protrude through the extended section 204a, i.e. at least some of the body portion extends below the top of the surrounding support surface. In some embodiments the body portion, e.g., the breast 104 is suspended in the open space under the extended section 204a such that a some portion, preferably a substantial portion or all of the volume to be treated is below the upper surface of the couch top 204 in the vicinity of the opening, and preferably such that a some portion, preferably a substantial portion or all of the area to be treated is below the lower surface of the couch top 204 in the vicinity of the opening. As such, physical and visual access to the breast 104 being treated is significantly enhanced. This is in contrast to conventional devices where a raised platform or cushion is placed onto a couch top and the breast is positioned above the couch top and the base supporting the couch top. The platform or cushion significantly limits the physical clearance for rotating a radiotherapy treatment machine around the patient. Physical and visual access to the breast being treated is also restricted by the presence of the couch base below the breast. It will be appreciated that visual access to the breast while beneficial is not necessary. Rather, as seen in FIG. 1 the present invention allows access by a radiation beam to some part of the body portion by virtue of allowing a beams-eye view of the portion (for example, by virtue of the portion being within or below the opening) without having to traverse through materials such as the support surface that could alter beam quality substantially. It will be appreciated that materials that do not affect beam quality substantially (or that affect the beam in an acceptable manner consistent with clinical goals) may be present, such as positioners or immobilizers such as low temperature thermoplastic materials, which may be used in conjunction with the present invention and may be integrally formed within the couch top 204 or may be separate accessories. If desired, a privacy shield in the form of panels, a box, lip, or cup, may be present. It will further be appreciated that as used herein, an "opening" refers to an opening broadly, which may be any shape, and fabricated in any manner. The opening may be a closed shape, such as circular, or may be an open shape, such as a generally U-shaped opening. The opening does not by necessity require that any portion of the patient support be removed during fabrication or use but rather may result from a contoured design that provides for the body part to extend through the support surface as described above.

Figure 2:
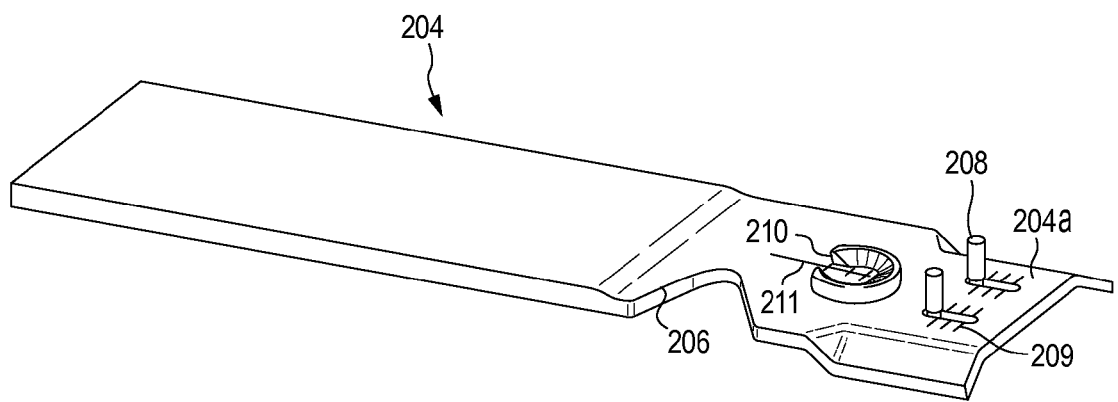
FIG. 2 is a schematic illustrating a couch top having an opening adapted to position a prone patient to receive radiotherapy of a breast in accordance with some embodiments of the invention.
Figure 3:
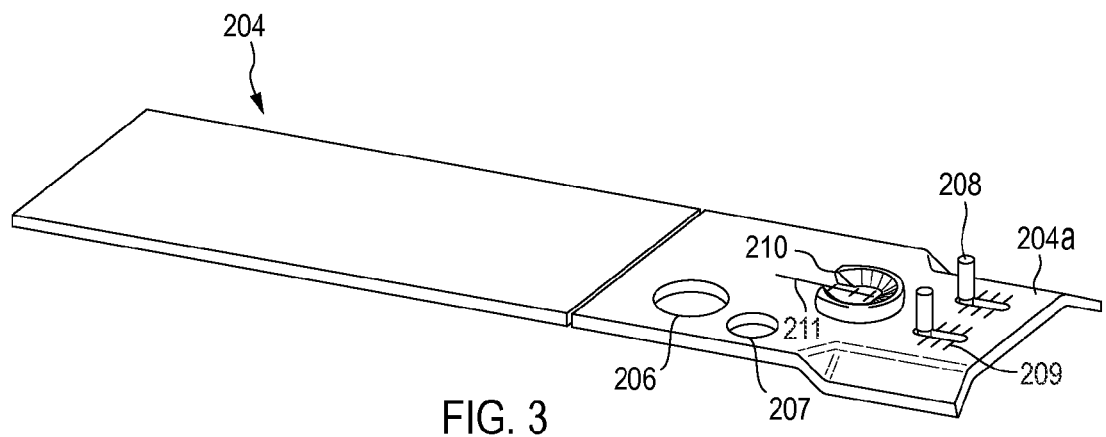
FIG. 3 is a schematic illustrating a couch top having a removable couch insert in accordance with some embodiments of the invention.

In some embodiments, the extended section 204a is an integral portion of the couch top 204 (FIG. 2). As such, the couch top 204 may be constructed as a single panel intended specifically for prone breast irradiation. In some embodiments, the extended section 204a is removable from the couch top 204 (FIG. 3). As such the extended section 204a may be constructed as a couch top insert and may be attached to a conventional couch top when in use. The couch top insert 204a may take the form of a reversible design to accommodate treatment of either the right or left breast. Alternatively, the couch top insert 204a may take the form of two separate top inserts, one for right handed the other left handed. The couch top insert 204a may be attached to a conventional couch top via various mechanisms. For example, the couch top insert may be placed on top of one or more support beams which may extend from and are engaged with a couch top frame. U.S. Pat. No. 5,778,047 discloses a radiotherapy couch top including a frame and one or more beams extending from the frame. The entire disclosure of U.S. Pat. No. 5,778,047 is incorporated herein by reference. The couch top insert may be connected to the support beams and thus the couch top frame by various connection mechanisms such as locking pins, latches or clamps etc. The support beams and/or couch top insert may have one or more discrete locations or may be indexed such that the couch top insert may be positioned accurately and repeatedly in the same indexed location during treatment cycles which may require multiple patient visits or treatment fractions. Other mechanisms may also be used to attach the couch top insert to a couch top. In some embodiments, the couch top 204 may include a first section and a second cantilevered section where the second cantilevered section connects to the first section in such a way as to leave an opening. The opening can be configured to allow a body portion to extend into or through as described above or below in connection with other embodiments.

Figure 4:
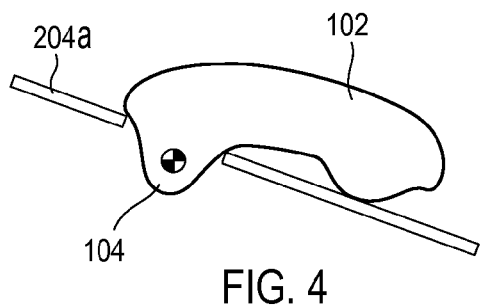
FIGS. 4 and 5 are schematics illustrating various configurations of couch top supporting surfaces in accordance with some embodiments of the invention.
Figure 5:
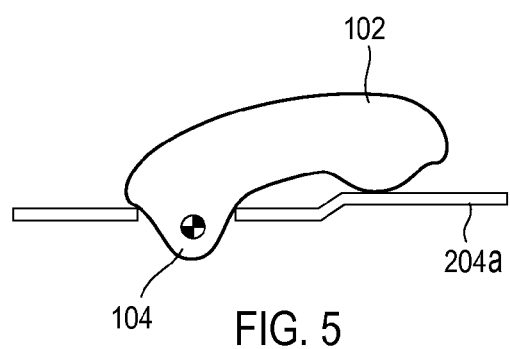
Figure 6:
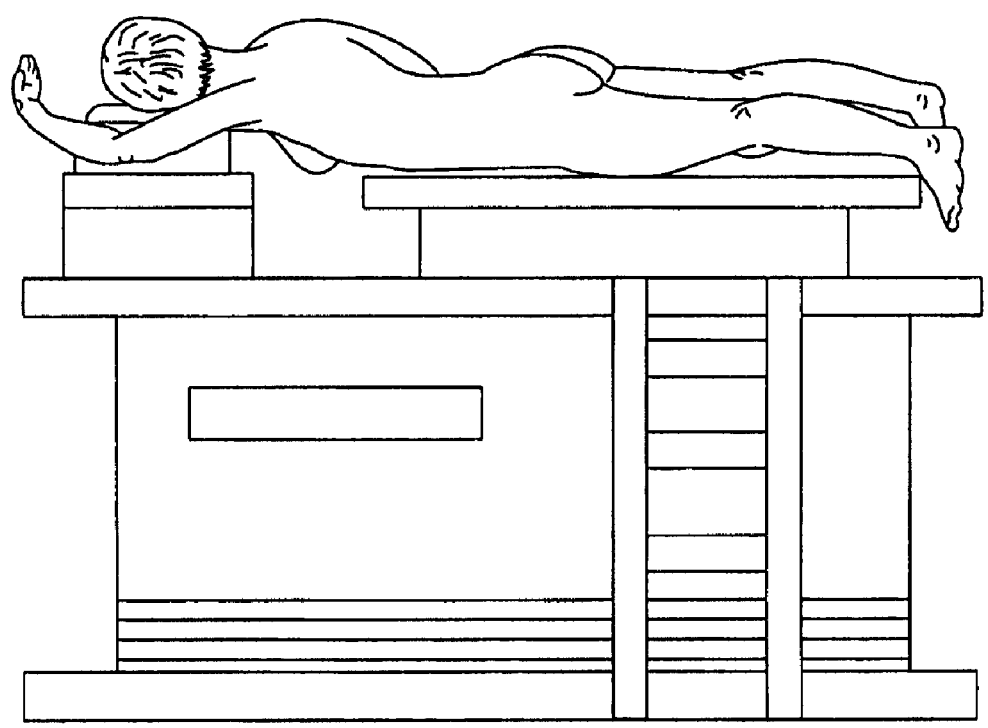
FIG. 6 is a schematic illustrating a conventional radiation treatment table for prone breast radiotherapy.

The couch top 204 and/or the extended section 204a may be tailored to patient's needs. For example, the extended section or the insert 204a may be ergonomically designed to provide comfort e.g. to a prone patient. The couch top 204 and/or the insert 204a may be curved or planar. The extended section or insert 204a may be angled or tilted (FIG. 4) to reduce pressure on the contralateral breast for comfort, and/or provide better access to the ipsilateral breast. Alternatively, the portion for receiving the contralateral breast may be elevated or angled (FIG. 5) to provide a radiation source with better access to the ipsilateral breast at small tangential angles. Padding may be placed on the supporting surfaces to provide comfort, and the contour of the padding in the opening area may be optimized to properly position the patient and improve comfort.

The opening 206 in the extended section 204a is configured to allow a body portion 104 to be treated to be exposed to radiation beams. By way of example, the opening 206 in the extended section 204a may be in U-shape to allow a prone patient's breast hanging into or through (FIG. 2). Alternatively, the opening 206 may be in O-shape to allow a prone patient's breast protruding into or through (FIG. 3). Other regular or irregular configurations of the opening may be formed. It will be appreciated that the opening 206 can be configured to allow a body portion to extend into but not necessarily through the opening. As such the radiation source 300 can be positioned below the extended section 204a to deliver a radiation beam upward, or obliquely upward, from below the opening to the body portion or at least a portion of the body portion. Alternatively, the opening 206 can be configured to allow a body portion e.g. a breast or a portion of the breast to extend through the opening. As such the radiation source 300 can either be positioned below the extended section to deliver a radiation beam upward, or obliquely upward, to the breast, or be positioned such to deliver a radiation beam to the breast or a portion of the breast at an angle that is substantially tangential to the patient's chest wall. The periphery of the opening 206 may be covered by padding of soft material to provide patient comfort. Thermoplastic immobilization materials may also be used in the opening 206 to assist in achieving desired tissue contour at the base of the body portion. In some embodiments, two or more openings may be formed in the extended section or couch top insert 204a. For example, the extended section or couch top insert 204a may includes a first opening 206 configured to allow a body portion hanging into or through and a second opening 207 configured to allow a treatment beam to pass through unimpeded for treatment of a different body portion such as tissue between a breast and an axilla or other tissue. This would allow treatment of different body portions without the need of repositioning of the patient. In some embodiments, the first or second openings may be filled with a removable insert to provide a patient supporting surface or to block radiation or beams if treatment of a different body portion is not needed. In some embodiments the second opening 207 is an extension of the first opening 206.

Immobilization devices may be provided in the extended section or couch top insert 204a. For example, structural features such as hand holds 208 may be provided and indexed, as shown at 209, for accurate positioning or repositioning. Face cushion 210, which may also be indexed, as shown at 211, may be provided to immobilize the patient's head and increase comfort. The face cushion 210 may be placed over an opening in the extended portion 204a allowing the patient to see and to breathe freely aiding comfort. Other structural features such as for retracting patient's shoulders or torso, while not shown in the drawings, may also be provided for positioning and/or immobilization. Low temperature thermoplastics may be used in the opening area to immobilize and/or position the body portion. It may be desirable to use a holder, cup, lip, box, protrusion, or other thermoplastic net or frame configured to support the breast and locate it accurately and repeatedly. The holder, cup, lip, box, protrusion or other thermoplastic net or frame etc. may be attached to or otherwise coupled to the lower surface of the extended section 204a in the vicinity of the opening via various means.

In some embodiments, the extended section 204a of the couch top may include one or more markers such as radio-opaque markers to aid in positioning in simulation and/or treatment. Optical markers may also be provided in the extended section for a camera to accurately track breathing motion of the patient in real time. This allows compensation of patient's breathing motion by various means during treatment such as by turning on or off the radiation source at specified intervals, thus effectively "freezing" the treatment volume in position.

The couch top 204 and/or couch top insert 204a may be constructed with any suitable radiation absorbing materials known in the art. Suitable radiation absorbing materials include, but are not limited to: lead, tungsten, tantalum, uranium, thorium, iridium, gold, iron, aluminum, and their alloys or mixtures or in binders that contain them including glass and plastic etc. Near the region of the body portion or breast being treated, the couch top 204 or insert 204a may be constructed with materials that have lower radiation absorption to allow penetration of the radiation to areas of interest such as the chest wall of the patient. In some embodiments, radiation absorbing materials are not required for construction of the couch top 204 or insert 204a and any strength bearing materials can be used. For instance, a radiation absorbing curtain or padding may be placed on the couch top and/or insert to block any unnecessary radiation of patient's healthy body parts. Alternatively, the patient 102 may wear a radiation protection uniform such as a lead lined hospital gown, shirt or apron to protect other healthy body parts.

In use, the patient 102 is placed on the couch top 204. The patient's upper body such as thorax, arm, and head is supported on the extended section 204a in a cantilevered manner. In cases where a removable couch top insert is used, the insert may be attached to the couch top and then the patient is placed on the couch top. The patient 102 is then properly positioned or repositioned based on a treatment plan using e.g. indexed structural features or markers. The prone breast 104 may be immobilized using thermoplastic net or frame. Once the patient is properly positioned and secured, imaging and/or treatment can be performed. The couch top or couch top insert of the invention supports various imaging and/or treatment options, including computed tomography (CT) or cone beam CT (CBCT), tomosynthesis, intensity-modulated radiation therapy (IMRT), image-guided radiation therapy, arc therapy, and 3-D arc therapy, and so on. The provided couch top or couch top insert may support a patient to receive whole-breast irradiation (WBI) or partial-breast irradiation (PBI). In some embodiments, an accelerator gantry may rotate in a vertical plane about a horizontal axis in positioning the treatment head and/or in delivery of treatment beams. During rotation of the gantry the treatment head may pass the open space under the extended section without obstruction or interference from the couch base or without obstruction from any frame or cushion elevated above the couch base. This would allow delivery of multiple radiation beams at various angles, including at small tangential angles, perpendicular angles with respect to the patient's chest wall, or at any angles therebetween.

A radiotherapy couch that is particular useful for supporting prone patients has been described. Those skilled in the art will appreciate that various other modifications may be made within the spirit and scope of the invention. All these or other variations and modifications are contemplated by the inventors and within the scope of the invention.

What is claimed is:

1. A radiotherapy couch, comprising:
   a base; and
   a couch top supported by the base, said couch top comprising a section extended in a cantilevered manner adapted to support a prone patient's upper body portion, said extended section being provided with a generally U-shaped opening configured to allow at least a portion of the upper body portion to extend into from above and to allow a radiation beam to pass through at an angle that is substantially tangential to a chest wall of the prone patient;
   wherein said extended section is removable from the couch top.

2. The radiotherapy couch of claim 1 wherein said extended section is an integral portion of the couch top.

3. The radiotherapy couch of claim 1 wherein said opening is formed by removing a portion of the extended section.

4. A radiotherapy couch top for supporting a patient to receive radiation therapy, comprising: a section to be supported in a cantilevered manner adapted to support a prone patient's upper body portion, said section being provided with a generally U-shaped opening configured to allow at least a portion of the upper body portion to extend into from above and to allow a radiation beam to pass through at an angle that is substantially tangential to a chest wall of the prone patient, wherein said section is detachable from the couch top.

5. The radiotherapy couch top of claim 4 wherein the portion of the upper body portion is a prone patient's breast.

6. The radiotherapy couch top of claim 5 wherein said section is detachable from the couch top and reversibly attachable to the couch top to allow at least a portion of the other breast hanging into.

7. The radiotherapy couch of claim 4 wherein the section has a second opening configured to allow a treatment beam to pass therethrough for treatment of a second portion of the upper body portion.

8. The radiotherapy couch top of claim 4 wherein said section is an integral portion of the couch top.

9. The radiotherapy couch top of claim 4 further comprising one or more immobilization devices in the section for positioning of the patient, wherein a location of at least one of the one or more immobilization devices is indexed.

10. A radiotherapy couch insert for positioning a body portion of a patient to receive radiation therapy, comprising: a section adapted to support a prone patient's upper body portion and a mechanism for attaching the section to a couch top of a radiotherapy couch to secure the section in a cantilevered manner, said section being provided with a generally U-shaped opening configured to allow at least a portion of the upper body portion to extend into from above and to allow a radiation beam to pass through at an angle that is substantially tangential to a chest wall of the prone patient.

11. The radiotherapy couch insert of claim 10 wherein the portion of the upper body portion extended into the opening is a prone patient's breast, said section has a first portion having the opening configured to allow the prone patient's breast hanging into, and a second portion configured to support the other breast, wherein the second portion is elevated with respect to the first portion to facilitate positioning of a radiation source in delivery of a radiation beam at an angle substantially tangential to a chest wall of the prone patient.

12. The radiotherapy couch insert of claim 10 wherein the portion of the upper body portion extended into the opening is a prone patient's breast.

13. The radiotherapy couch insert of claim 10 further comprising one or more immobilization devices in the section for positioning of the patient, wherein a location of at least one of the one or more immobilization devices is indexed.

14. A radiation method comprising:
positioning a patient in a prone position on a couch top, said couch top comprising a removable section extended in a cantilevered manner, said removable section having an upper surface adapted to support an-upper body portion of the patient, a lower surface, and an opening configured to allow at least a portion of the upper body portion to extend to or below the lower surface in the vicinity of the opening;
positioning a radiation source relative to the portion of the upper body portion; and
delivering a therapeutic radiation beam from the radiation source to at least a portion of the portion extended to or below the lower surface in the vicinity of the opening.

15. The radiation method of claim 14 wherein said positioning of a radiation source comprising positioning a linear accelerator housed in a gantry relative to the portion of the upper body portion.

16. The radiation method of claim 15 further comprising moving the gantry below the section to allow delivery of a radiation beam from below the portion of the upper body portion extended to or below the lower surface.

17. The radiation method of claim 14 wherein the positioning a radiation source step comprising positioning the radiation source below the opening to provide a beam's-eye view of the portion of the upper body portion without traversing through materials of the section.

18. A radiotherapy couch, comprising:
a base; and
a couch top supported by the base, said couch top having a first section, a second cantilevered section, and an opening in the cantilevered section or between the cantilevered section and the first section, said cantilevered section having an upper surface configured to support a body portion and a lower surface, said opening being configured to allow at least a portion of the body portion to extend to or below the lower surface in the vicinity of the opening to receive external therapeutic radiation beams from below the opening;
wherein the second cantilevered section is removable from the first section.

19. The radiotherapy couch of claim 18 wherein the opening is generally U-shaped.

20. The radiotherapy couch of claim 18 further comprising a structure coupled to the lower surface of the cantilevered section in the vicinity of the opening for positioning and/or immobilizing the portion of the body portion extended below the lower surface.

21. A radiotherapy system, comprising:
a couch, comprising:
a base; and
a couch top supported by the base, said couch top having a first section, a second cantilevered section, and an opening in the cantilevered section or between the cantilevered section and the first section, said cantilevered section having an upper surface configured to support a body portion and a lower surface, said opening being configured to allow at least a portion of the body portion to extend to or below the lower surface in the vicinity of the opening; and
a radiation source operable to deliver a therapeutic radiation beam to at least a portion of the portion extended to or below the lower surface in the vicinity of the opening, wherein the radiation source is operable to rotate in a vertical plane that includes an axis passing through the opening.

22. The radiotherapy system of claim 21 wherein said radiation source comprises a linear accelerator.

23. The radiotherapy system of claim 21 wherein said radiation source is operable to deliver a radiation beam upward from below the opening to at least a portion of the portion extended to or below the lower surface in the vicinity of the opening.

24. The radiotherapy system of claim 21 wherein said radiation source is operable to deliver a radiation beam obliquely upward to at least a portion of the portion extended to or below the lower surface in the vicinity of the opening.

25. The radiotherapy system of claim 21 wherein the radiation source is operable to be positioned below the cantilevered section to provide a beam's-eye view of the portion of the body portion extended to or below the lower surface in the vicinity of the opening without traversing through materials of the cantilevered section.

\* \* \* \* \*